US00PP18693P2

(12) United States Plant Patent
Bradford

(10) Patent No.: US PP18,693 P2
(45) Date of Patent: Apr. 1, 2008

(54) NECTARINE TREE NAMED 'SUGARRED I'

(50) Latin Name: *Prunus persica*
Varietal Denomination: SUGARRED I

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,894

(22) Filed: Dec. 13, 2006

(51) Int. Cl.
*A01H 5/00* (2006.01)

(52) U.S. Cl. ..... Plt./187
(58) Field of Classification Search ..... Plt./187
See application file for complete search history.

(56) References Cited

U.S. PATENT DOCUMENTS

PP7,507 P * 4/1991 Bradford et al.

* cited by examiner

*Primary Examiner*—Kent Bell

(57) ABSTRACT

The present invention relates to a new and distinct variety of nectarine tree, *Prunus persica,* broadly characterized by a medium size, moderately vigorous, hardy, self-fertile, productive and regular bearing tree. The fruit matures under the ecological conditions described in mid June, with first picking on Jun. 19, 2006. The fruit is uniformly large in size, mildly acidic and sweet in flavor, globose in shape, clingstone in type, very firm in texture, yellow with strong red bleeding in flesh color, and full red in skin color.

1 Drawing Sheet

Botanical classification: *Prunus persica.*
Variety denomination: 'Sugarred I'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'SUGARRED I'. The present variety was hybridized by me in 2000, grown as a seedling on its own root in my greenhouse, and transplanted to a cultivated area of my experimental orchard located near Le Grand, Calif., in Merced County (San Joaquin Valley).

The variety was developed as a first generation cross using 'Spring Bright' (U.S. Plant Pat. No. 7,507), nectarine as the selected seed parent and an unnamed nectarine seedling as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to its selected seed parent, 'Spring Bright' nectarine, by producing nectarines that are nearly globose in shape, acidic and sweet in flavor, and full red in skin color, but is distinguished therefrom by producing nectarines that are yellow with much more red bleeding in flesh color, that are larger in size, and that mature about five days earlier.

SUMMARY OF VARIETY

In summary, the present variety is characterized by a medium size, moderately vigorous, hardy, self-fertile, productive and regular bearing tree. The fruit matures under the ecological conditions described in mid June, with first picking on Jun. 19, 2006. The fruit is uniformly large in size, mildly acidic and sweet in flavor, globose in shape, clingstone in type, very firm in texture, yellow with strong red bleeding in flesh color, and full red in skin color.

DRAWING

The accompanying photograph consists of four whole fruits positioned to display the characteristics of the skin color and form, one fruit divided transversely to the suture plane to reveal the flesh and stone, two insets to reveal buds and blossoms in various stages, various leaves, a clean dry stone, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 23, 2006, on the original tree during its sixth growing season. All major color code designations are by reference to the Inter-Society Color Council, National Bureau of Standards. Common color names are also used occasionally.

Tree

Size: Medium, reaching and maintaining a height of 8' [2.44 m.] and a spread of 7' [2.13 m.] after six growing seasons utilizing typical dormant pruning.

Vigor: Moderate, responding typically to irrigation and fertilization. The variety grows about 3' [0.91 m.] of surplus top-growth during the spring and summer. The plant should be grown on a standard commercial rootstock for production purposes.

Growth: Spreading and dense.
Form: Pruned to a perpendicular "V".
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning necessary.
Fertility: Self-fertile.
Bearing: Regular bearer with no alternate bearing yet observed.
Approximate chilling requirement: 525 hours.
Trunk:
*Size.*—Medium, reaching a maximum diameter of 3½" [89 mm.] after the sixth growing season.
*Texture.*—Shaggy.
*Bark color.*—A Grayish olive [110. gy.Ol] and Dark brown [59. d.Br] variegation.
*Lenticels.*—Approximate Number Per Square Inch: 8. Color: Moderate orange yellow [71. m.OY]. Typical Size: 3/16" [4.8 mm.] to 7/16" [11.1 mm.]. Shape: Eye-shaped to elongated.
Branches:
*Size.*—Diameter of limb is 2⅛" [54 mm.] measured 12" above the crotch, 1 5/16" [33 mm.] measured 12" above the first fork.
*Texture.*—Smooth on first and second year wood, increasing roughness with age.
*Color.*—1st Year Wood Topside: Grayish red [19. gy.R]. 1st Year Wood Underside: Brilliant yellow green [116. brill.YG]. Older Wood: Deep yellowish brown [75. deep yBr].
*Lenticels.*—Number Per Square Inch: More than 60 on second year wood. Color: Light yellowish brown [76. l.yBr]. Typical size: 1/64" [0.4 mm.] to 3/32" [2.4 mm.] on second year wood. Shape: Elongated.
Leaves:
*Size.*—Medium. Average Length: 5⅜" [137 mm.]. Average Width: 1½" [38 mm.].
*Arrangement.*—Alternate.
*Thickness.*—Medium.
*Form.*—Elliptical.
*Apex.*—Acuminate.
*Base.*—Rounded to acute.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Vein color.*—Light greenish yellow [101. l.gY].
*Petiole.*—Average Length: ⅜" [9.5 mm.]. Average Thickness: 1/16 [1.6 mm.]. Color: Moderate yellow green [120. m.YG].
*Stipules.*—Number: 2 per leaf, up to 6 per growing tip. Average Length: ⅜" [9.5 mm.]. Color: Brilliant yellow green [116. brill.YG]becoming Moderate reddish brown [43. m.rBr] with maturity.
*Glands.*—Number: Usually 2 per leaf. Position: Slightly alternate, positioned at the intersection of the petiole and the base of the leaf. Size: Small. Form: Globose. Color: Strong yellow green [117. s.YG] becoming Moderate yellow brown [77. m.yBr] with age.
*Leaf buds.*—Pointed, medium in size.

Flower buds:
*Hardiness.*—Hardy, with respect to central California winters.
*Diameter.*—Typically ⅜" [9.5 mm.] 1 week before bloom.
*Length.*—Typically 11/16" [17.5 mm.] 1 week before bloom.
*Form.*—Not appressed.
*Surface.*—Pubescent.
*Color.*—Light purplish pink [249. l.pPk].
Flowers: Perfect, complete, perigynous, usually a single pistil, typically thirty or more stamens, five and sepal and petal locations alternately positioned.
*Type.*—Showy, very large.
*Average flower diameter.*—2" [50.8 mm.].
*Number of petals.*—Usually five, some with extra petal fragments and some double blossoms observed.
*Petal shape.*—Circular to oval.
*Petal margin.*—Somewhat wavy.
*Average petal diameter.*—13/16" [20.6 mm.].
*Average petal length.*—13/16" [20.6 mm.].
*Petal apex.*—Rounded.
*Petal base.*—Rounded to somewhat truncate.
*Petal color.*—Pale pink [7. p.Pk] toward the apex, Light pink [4. l.Pk] toward the base.
*Anther color.*—Dark red [16. d.R] over a Light yellow [86. l.Y] center at bloom onset.
*Stigma color.*—Light greenish yellow [101. l.gY].
*Sepal color.*—Dark purplish red [259. d.pR].
*Sepal length.*—5/16" [7.9 mm.].
*Sepal width.*—¼" [6.4 mm.].
*Average pistil length.*—13/16" [20.6 mm.].
*Average stamen length.*—11/16" [17.5 mm.].
*Fragrance.*—Moderate.
*Blooming period.*—Medium, close to 'Spring Bright' (U.S. Plant Pat. No. 7,507) nectarine.
*Onset of bloom.*—One percent on Feb. 23, 2006.
*Date of full bloom.*—Mar. 8, 2006.
*Duration of bloom.*—One to two weeks, dependent on ambient temperature.
*Number per cluster.*—1 to 3 with single flowers most common.

FRUIT

Maturity when described: Firm ripe, Jun. 23, 2006.
Date of first picking: Jun. 19, 2006.
Date of last picking: Jun. 29, 2006.
Size: Uniform, large.
*Average diameter axially.*—3 1/16" [78 mm.].
*Average diameter across check plane.*—2 15/16" [75 mm.].
*Average diameter across cheek plane.*—3 1/16" [78 m.].
*Typical weight.*—8.2 ounces [232 grams].
Form: Uniform, globose, slightly asymmetrical.
*Longitudinal section form.*—Round to elliptical.
*Axial view.*—Round with a slight hump at the suture.
Suture: A very sharp groove near the base, a shallow rough along the side, and a sharp groove toward the apex, ending just beyond the pistil point with a moderate depression.
Ventral surface: Rounded, lipped stronger toward the apex.
Lips: Slightly unequal.
Cavity: Flaring, circular, suture usually showing on both sides, Strong orange yellow [68. s.OY] stem markings typical.
*Depth.*—½" [12.7 mm.].
*Breadth.*—1 1/16" [27.0 mm.].

Base: Truncate.
Apex: Rounded.
Pistil point: Both apical and oblique, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Moderately astringent.
*Tendency to crack.*—Slight.
*Color.*—Dark red [16. d.R] smoothly blending into a Strong reddish orange [35. s.rO] background with the slightest amount of Pale orange yellow [73. p.OY] freckling.
Flesh:
*Color.*—Deep red [13. deep R] toward the skin finally blending into Brilliant orange yellow [67. brill.OY] close to the stone.
*Surface of pit cavity.*—Deep red [13. deep R] broken fibers when twisted from stone.
*Amygdalin.*—Abundant.
*Juice.*—Abundant, rich.
*Texture.*—Very firm, crisp.
*Fibers.*—Abundant, fine.
*Ripens.*—Slightly earlier at the apex.
*Flavor.*—Acidic and sweet, typically 15 brix.
*Aroma.*—Moderate.
*Eating quality.*—Excellent.

STONE

Type: Clingstone.
Form: Oval.
Hilum: Oblong.
Base: Straight oblique.
Apex: Rounded to obtuse with an average angle of 110 degrees.
Sides: Equal.
Surface: Regularly furrowed toward the apex, pitted toward the base.
Ridges: Jagged.
External color: Moderate yellowish brown [77. m.yBr] when dry.
Pit wall color when cracked: Light yellowish brown [76. l.yBr].
Cavity surface color: Deep brown [56. deep Br].
Average pit wall thickness: ¼" [6.4 mm.].
Average width: 1 7/16" [36.5 mm.].
Average length. 1⅛" [28.6 mm.].
Average breadth: ¾" [19.1 mm.].
Tendency to split: Slight.
Kernel:
*Form.*—Oval.
*Skin color.*—Strong yellowish brown [74. s.yBr] when dry.
*Pellicle color.*—Grayish brown [61. gy.Br].
*Vein color.*—Dark brown [59. d.Br].
*Taste.*—Sweet.
*Viable.*—Yes.
*Average width.*—9/16" [14.3 mm.].
*Average length.*—¾" [19.1 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, It is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected seed parent, 'Spring Bright' (U.S. Plant Pat. No. 7,507) nectarine, by producing nectarines that are nearly globose in shape, acidic and sweet in flavor, and full red in skin color, but is distinguished therefrom by producing nectarines that are yellow with much more red bleeding in flesh color, that are larger in size, and that mature about five days earlier.

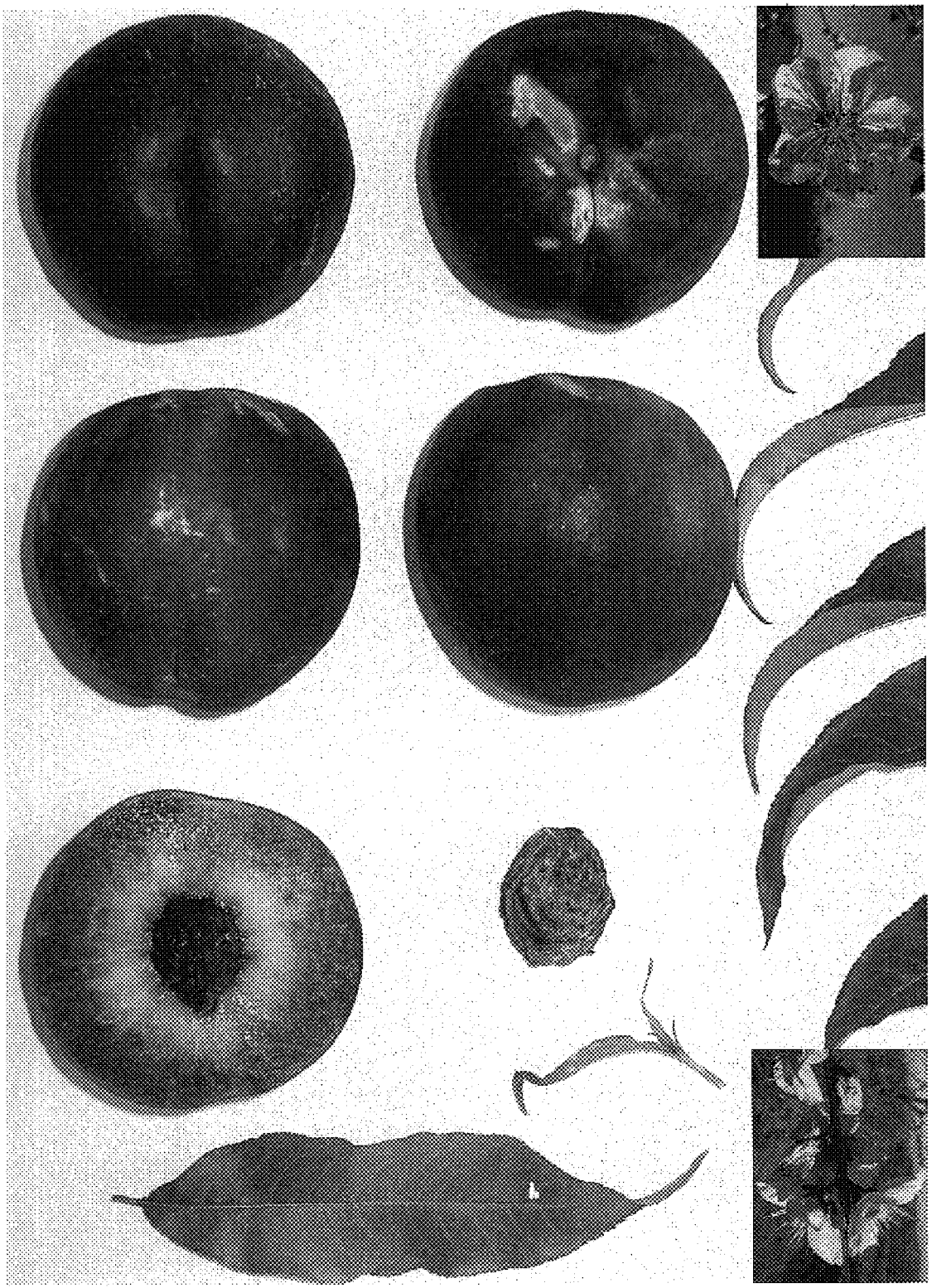

* * * * *